(12) United States Patent
Prins et al.

(10) Patent No.: US 8,084,270 B2
(45) Date of Patent: Dec. 27, 2011

(54) DEVICE FOR ANALYZING FLUIDS

(75) Inventors: Menno Willem Jose Prins, Rosmalen (NL); Ralph Kurt, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 707 days.

(21) Appl. No.: 12/161,715

(22) PCT Filed: Jan. 15, 2007

(86) PCT No.: PCT/IB2007/050121
§ 371 (c)(1),
(2), (4) Date: Jul. 22, 2008

(87) PCT Pub. No.: WO2007/085980
PCT Pub. Date: Aug. 2, 2007

(65) Prior Publication Data
US 2010/0233822 A1      Sep. 16, 2010

(30) Foreign Application Priority Data
Jan. 25, 2006 (EP) .................................. 06100815

(51) Int. Cl.
G01N 1/00       (2006.01)
G01N 33/553     (2006.01)
G01N 33/50      (2006.01)
G01N 21/01      (2006.01)

(52) U.S. Cl. .................. 436/174; 422/82.05; 422/82.08; 422/82.09; 422/502; 422/504; 435/287.2; 436/86; 436/94; 436/526

(58) Field of Classification Search .......... 366/273–274; 422/82.05, 82.08–82.09, 502, 504; 435/287.2, 435/288.3, 288.5; 436/86, 94, 149, 174, 436/526
See application file for complete search history.

(56) References Cited

U.S. PATENT DOCUMENTS

| | | | | |
|---|---|---|---|---|
| 3,799,742 A * | 3/1974 | Coleman ........................ | 422/417 |
| 5,019,272 A * | 5/1991 | Kurahashi et al. ............. | 210/695 |
| 5,222,808 A * | 6/1993 | Sugarman et al. ............. | 366/274 |
| 5,443,791 A * | 8/1995 | Cathcart et al. ................. | 422/65 |
| 5,514,340 A * | 5/1996 | Lansdorp et al. .............. | 422/534 |
| 6,096,563 A * | 8/2000 | Hajizadeh et al. ............. | 436/523 |
| 6,159,689 A * | 12/2000 | Parton ................................ | 435/5 |
| 6,197,595 B1 * | 3/2001 | Anderson et al. .............. | 436/180 |
| 6,420,114 B1 * | 7/2002 | Bedilion et al. ................... | 435/6 |
| 6,440,725 B1 * | 8/2002 | Pourahmadi et al. ...... | 435/288.5 |
| 6,635,493 B2 | 10/2003 | Van Damme et al. | |
| 6,736,978 B1 | 5/2004 | Porter et al. | |

(Continued)

FOREIGN PATENT DOCUMENTS
EP           1327473 A1     7/2003
(Continued)

OTHER PUBLICATIONS

Barbic, M, Journal of magnetism and Magnetic Materials 2002, 249, 357-367.*

(Continued)

Primary Examiner — Arlen Soderquist

(57) ABSTRACT

It is an object of the invention to provide for an alternative for analyzing fluids. To this end a device for analyzing fluids comprising magnetic particles is provided, the device comprising magnetic means for generating a magnetic field designed for exerting a magnetic force to the magnetic particles creating a movement of the fluid comprising targets and a membrane with an array for moving the fluid through or along the array.

21 Claims, 6 Drawing Sheets

U.S. PATENT DOCUMENTS

| | | | |
|---|---|---|---|
| 6,988,825 B2 * | 1/2006 | Coville et al. | 366/273 |
| 7,364,350 B2 * | 4/2008 | Coville et al. | 366/273 |
| 7,892,427 B2 * | 2/2011 | Barbic et al. | 210/222 |
| 2002/0015959 A1 * | 2/2002 | Bardell et al. | 435/6 |
| 2003/0134316 A1 * | 7/2003 | Tashiro et al. | 435/6 |
| 2004/0021073 A1 * | 2/2004 | Barbic et al. | 250/298 |
| 2004/0023273 A1 | 2/2004 | Puget et al. | |
| 2004/0115709 A1 | 6/2004 | Morozov et al. | |
| 2005/0009004 A1 | 1/2005 | Xu et al. | |
| 2005/0048673 A1 | 3/2005 | Baudry et al. | |
| 2005/0074784 A1 | 4/2005 | Vo-Dinh | |
| 2005/0170418 A1 | 8/2005 | Moreland et al. | |
| 2006/0166377 A1 * | 7/2006 | Fredriksson et al. | 436/526 |
| 2008/0185043 A1 * | 8/2008 | Prins et al. | 137/2 |

FOREIGN PATENT DOCUMENTS

| | | |
|---|---|---|
| WO | WO0227312 A1 | 4/2002 |
| WO | WO2004102152 A2 | 11/2004 |
| WO | WO2005072855 A1 | 8/2005 |
| WO | WO2006079998 A1 | 8/2006 |

OTHER PUBLICATIONS

Wirix-Speetjens, R. et al, IEEE Transactions on Magnetics 2005, 41, 4128-4133.*

Graham et al: "Single Magnetic Microsphere Placement and Detection On-Chip Using Current Line Designs With Integrated Spin Valve Sensors: Biotechnological Applications"; Journal of Applied Physics, vol. 91, No. 10, May 15, 2002, pp. 7786-7788.

* cited by examiner

DEVICE FOR ANALYZING FLUIDS

The invention relates to a device for analyzing fluids, a control device for directing magnetic particles and fluid through different parts of a membrane of a device and to a method for analyzing fluids.

For the detection of so called targets in various fluids devices are developed more and more for different applications. As examples for targets nucleic acids, antibodies, antigens, receptors, haptens, or ligands are named. Further targets are proper for detection by a device, e.g. cell fragments, viruses, or substances within food fragments. Targets often are molecules, in this case also called molecular species. As examples for fluids comprising targets blood, saliva, urine, tissue extract, interstitial fluid, food extract, and environmental samples are named. Further fluids are proper for comprising targets to be detected. The fluid can be taken directly from the source without treatment, but may also first undergo one or more pretreatment steps, e.g. filtration, dissolution, grinding, purification, concentration, dilution, amplification. A device in the sense used in this invention is a device incorporating little amounts of substances. The term device in the sense of this invention further comprises microdevices and microfluidic devices. For example the device comprises biochips, also called biosensor chips, biological microchips, gene chips or DNA chips, which consist in their simplest form of a substrate on which a large number of different probe molecules are attached, on well defined regions on the chip, to which molecules or molecule fragments to be analyzed within the substance or fluid bind if matching. The substrate may be designed as a porous material or a membrane through which the substance or fluid are transported. For example, a fragment of a single stranded DNA molecule binds to one unique complementary DNA strand (c-DNA) fragment. The occurrence of a binding reaction can be detected, e.g. by using fluorescent, chemiluminescent, radioactive or absorptive markers that are coupled to the molecules to be analyzed. This provides the ability to analyze small amounts of a large number of different molecules or molecular fragments in parallel within a short time. One biochip can hold assays to be analyzed, here referred to as fluids 3, for a few up to 1000 or more different molecular fragments. For reason of transporting and mixing the substance or fluid incorporated in the device is pumped through the device by micropumps. This pumping of the fluid in the device can also be used for conveying the fluid repeatedly along the substrate or through the membrane, respectively. By pumping, the probability that a target reaches the probe molecules is increased and specific binding of the targets within the fluid to the probe molecules attached to the membrane is improved. The provision of micropumps in devices is difficult to manufacture, pretty expensive, and susceptible to failure. Using a device 1 with micropumps a large dead volume of fluid occurs, this means essential parts of the fluid are not approachable to analysis. Therefore, large amounts of fluids incorporating targets are necessary, which contribute to costs, time, and sample-taking disadvantages.

It is an object of the invention to provide for an alternative for analyzing fluids.

This object is solved by a device for analyzing fluids comprising magnetic particles, the device comprising magnetic means for generating a magnetic field designed for exerting a magnetic force to the magnetic particles creating a movement of the fluid comprising targets. Further, a control device is provided for directing magnetic particles and fluid through different parts of a membrane of a device comprising means for varying the magnetic field strength of magnetic means to the end of directing the magnetic particles and the fluid through the device. Moreover, a method for analyzing fluids comprising magnetic particles is made available, comprising the steps of generating a magnetic field for exerting a magnetic force to the magnetic particles, thereby exerting a magnetic force to the magnetic particles to the end of creating a movement of the fluid. A force on the magnetic particles is achieved by applying a magnetic field and/or a magnetic field gradient.

Thus, moving of fluids through a device for analyzing purposes is realized in a straightforward way.

The invention realizes transport of fluid without mechanical means and is suitable for small volumes of fluid, which may contain complex biological mixtures. Moving of the fluid is caused by drag forces of the magnetic particles on the surrounding fluid comprising the target. It is important to mention that the fluid is moved by the magnetic particles and essentially no forces act on the fluid directly. The invention offers analyzing with small volume of fluid as samples, a compact design with small cartridge, it provides high speed analyzing at low costs and a high reliability.

Further means for moving the fluid are combinable with the inventional features creating a movement of the fluid.

Some embodiments of the invention are described in the dependent claims.

One embodiment discloses a membrane with an array of binding spots for moving the fluid through the membrane and for binding a target to the binding spots, i.e. the capture molecules. The combination of movement of the fluid with a porous membrane inside the device makes the improved and faster passing of fluid through the membrane possible.

In a further embodiment the device comprises a magnetic field changing its direction and/or magnitude in time in a predefined way extending essentially perpendicular to each other controlled by a control device varying the magnetic forces exerted to the magnetic particles for directing the magnetic particles and the fluid through the device. The magnetic fields are for instance generated by horizontally arranged or vertically arranged magnetic means relating to the position of the device. Further magnetic fields are applicable, especially a magnetic field arranged perpendicular to the two magnetic fields establishing a magnetic field in each direction in space. The fluid is freely transported through the device in different directions. An improved mixing and binding of substances or targets within the fluid in the device is achieved. A force and therefore a movement of the magnetic particles or beads can be achieved by applying a magnetic field gradient. The control device is in a further embodiment designed to direct the magnetic particles and the fluid through different parts of the membrane. Mainly, this supports the binding of different substances, referred to as targets, to each other which have a distant location in fluid and membrane, especially in the case of several targets. Targets in fluid are brought to substances in the membrane, for instance incorporated in binding spots, for establishing a unique binding.

A further variation of the embodiment above discloses a control device designed to direct the magnetic particles and the fluid on one side of the membrane through the membrane from a first direction, along the membrane in a second direction, on the opposed side of the membrane through the membrane from a third direction in the reverse direction to the first direction, and along the membrane in a fourth direction in the reverse direction to the second direction, thereby creating a circular flow of the magnetic particles and the fluid.

In another embodiment a plurality of the magnetic particles form multi-particle structures or strings for improving the movement of fluid through the device. A multi-particle structure is much more accessible to magnetic forces than a structure out of single magnetic particles. Thus, higher forces to the magnetic particles are generated and higher drag forces of the magnetic particles acting on the fluid for moving the fluid. The multi-particle structures can be formed under the influence of magnetic or other forces, e.g. chemical. An advantage of using magnetic forces is that multi-particle structures can be reversibly assembled and dissembled under the influence of an applied magnetic field.

For sake of measuring the amount or concentration of a substance in the fluid a magnetic field generating wire or coil is provided for generating a magnetic field inducing a magnetic stray field of the magnetic markers and a Giant Magneto Resistive sensor for measuring the magnetic stray field. This measurement is preferably done after termination of the movement by the magnetic means. The magnetic particles creating a movement of the fluid may be identical to the markers inducing a magnetic stray field. Otherwise the magnetic particles creating a movement of the fluid and the targets inducing a magnetic stray field are different and not integrated in one item.

An alternative measuring of the amount or concentration of a substance in the fluid is achieved by an optical detector for optical detection of the targets or of markers, and so measuring the amount of targets. The advantage is that common optical labelling techniques can be used, e.g. labelling with fluorophore markers.

Preferably, magnetic particles are moved out of the membrane or at least out the analyzed regions and away from the viewing field before the optical detection process for analyzing the fluid takes place, in order to avoid unwanted background signals from the particles, referred to as light scattering, absorption, or luminescence.

Examples of possible membranes are porous aluminum or aluminumoxide, silicon or silicon oxide (with or without electrodes), plastic membranes, e.g. nylon, membranes based on fibrous material, e.g. nitrocellulose.

In an alternative of the invention, current conducting wires are integrated into or onto the membrane for the generation of magnetic fields.

In an alternative of the invention a mechanical stabilizer is arranged at the membrane for improving mechanical stability of the membrane. If a large quantity of magnetic particles or beads are inside the membrane, the magnetic field will also induce forces at the membrane. The mechanical stabilizer can be designed as a support membrane, for instance a wire grid or a stable ceramic substrate build as thin layer attached to the membrane of the device. Alternatively, stiff porous substrate material could be used as e.g. described in U.S. Pat. No. 6,635,493.

An alternative provides the magnetic particles designed as markers for optical detection, preferably luminescent, fluorescent or phosphorescent markers. Then, the magnetic particles are bound to the targets directly or via counter particles. Counter particles are particles specifically bound uniquely to one kind of particles. In this case the particles consequently have at least the function to move the fluid and also to be detected for the reason of measuring the amount of targets.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 1 shows a schematic device of the state of the art comprising a micropump for pumping fluid through a membrane incorporated in the device, FIG. 2 shows another schematic device illustrating a drop of fluid incorporating targets brought to binding spots at an array for binding the targets to its corresponding binding spot, FIG. 3 shows a schematic view of the principle of binding a target to a substrate by complementary binding sites with a marker coupled to the target, FIG. 4 shows a schematic view similar to FIG. 3 with a different target binding to different complementary binding sites, with a marker coupled to the target, FIG. 5 shows an exemplary schematic side view of a device with two horizontal magnetic means over and below the device for generating a magnetic field or magnetic field gradient applied to magnetic beads forcing also the fluid to flow or move, and increases thereby the probability that a target bounds to a detection site and to the end allowing measuring the target concentration in the fluid, FIG. 6 shows a schematic side view similar to FIG. 5 with four magnetic means arranged at the device for controllably directing the fluid through the device.

Figure 1:
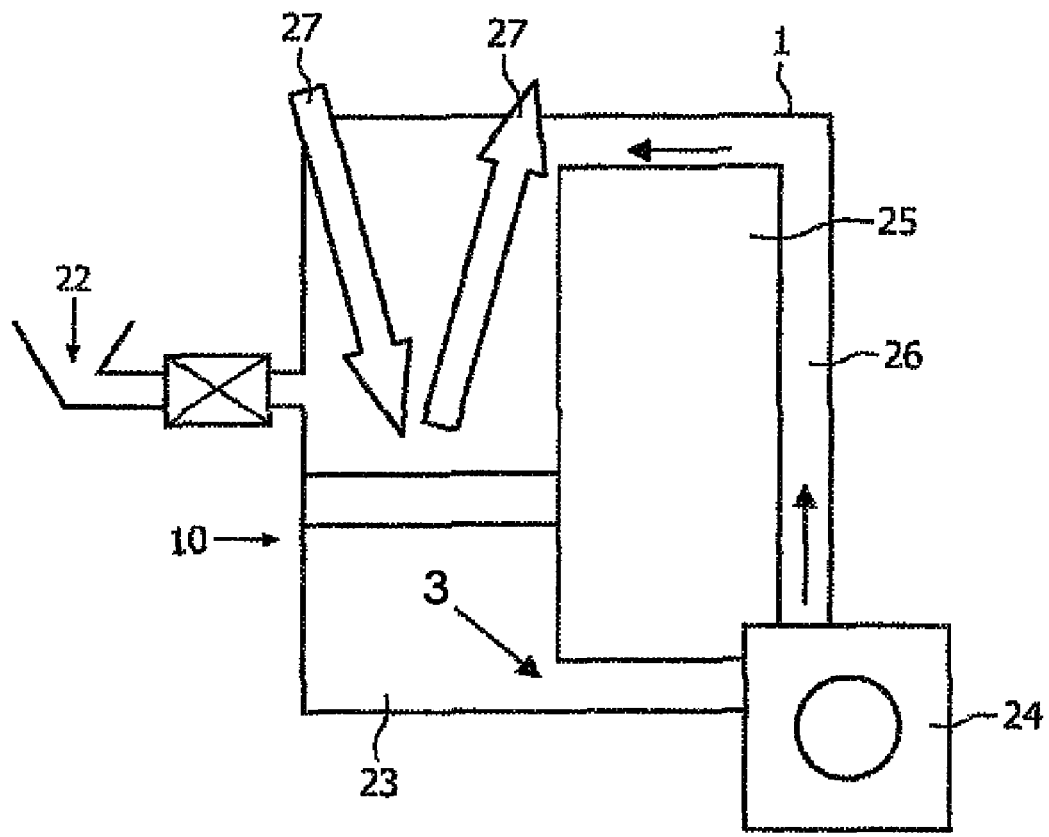

FIG. 1 shows a scheme of a state of the art device 1 for analyzing substances, essentially fluids 3 originating from human or animal sources, for instance blood, saliva, urine. The term substance is therefore replaced by the term fluid 3 in the following. The fluid 3 comprises targets 30a, 30b to be analyzed. The term microfluid device is by definition incorporated by the term device 1. The device 1 comprises a housing incorporating a chamber 23 for accommodating the fluid 3. Within the chamber 23 a barrier 25 projects through the whole height of the device 1 providing ducts 26 in the chamber 23 enabling a circular fluidic flow. The device 1 has an intake 22 for admitting the fluid 3 to the chamber 23 in the inside of the device 1. A micropump 24 is provided in the device 1 for exerting a pressure to the fluid 3 thereby generating a circular flow of the fluid 3 inside the device 1 around the barrier 25. The micropump 24 permanently pumps fluid 3 along and around the barrier 25 through the device 1 as long as the analyzing process in ongoing. This pumping is typically done in steps as hybridization, which demands some time. Moreover, micropumping of fluids is applied when dedicated temperature cycles are required. After a number of pumping and hybridizations steps analysis of the fluid is executed, especially optical analyzing. A membrane 10 is arranged between the inner side of the housing of the device 1 and the barrier 25 projecting through the whole height of the chamber 23 of the device 1 and dividing the chamber 23 in two parts. Membrane 10 is designed porous to enable flow of the fluid 3 through the membrane 10. Membrane 10 is one essential feature in the device 1 comprising binding spots 32a, 32b which comprise complementary binding sites 31a, 31b for binding targets 30a, 30b to the membrane 10, as will be described below. Ideally, the targets 30a, 30b bind exclusively to complementary binding sites 31a, 31b within the binding spots 32a, 32b, respectively, at the membrane 10, the targets 30a, 30b are fixed to their complementary binding sites 31a, 31b after binding. Ideally, a binding only occurs when a special target 30a, 30b exactly fits to its complementary binding site 31a, 31b. By passing through the membrane 10 targets 30a, 30b within the fluid 3 to be analyzed bind to binding spots 32a, 32b at the membrane 10. The passing of the fluid 3 through the membrane 10 is repeated several times enhancing the binding rate of targets 30a, 30b to the binding spots 32. The arrows 27 in FIG. 1 pointing in the direction of the membrane 10 and in the opposite direction indicate the irradiation, i.e. excitation of the optical marker 33, and reflection/fluorescence, i.e. the optical response, of light onto the membrane 10. Optical markers 33 are attached to the targets 30a, 30b bound to the binding spots 32, which can be detected by an optical detector (not shown) receiving the light beams irradiating onto the optical markers 33. By means of measuring the optical markers 33 the amount of the targets 30a, 30b bound at the membrane 10 each being bound to one marker 33 are determined. This process allows for measuring the amount of targets 30a, 30b within the fluid 3.

Figure 2:
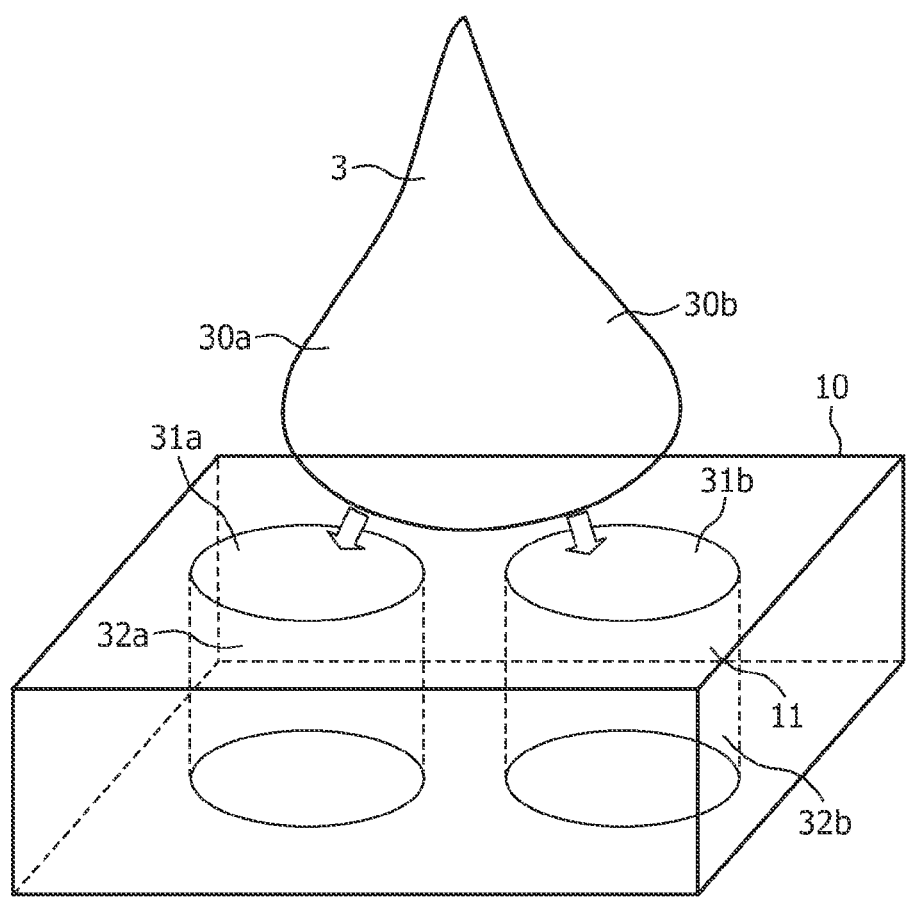

FIG. 2 shows a schematic view of the principle of binding a target 30a, 30b to a substrate or membrane 10 by complementary binding sites 31a, 31b within an array 11 with a marker 33 coupled to the target 30a, 30b for detection of targets 3 as described in FIG. 1. The kind of binding assay described is only by way of example, the membrane 10 can be designed with further features for conducting for example unbinding, displacement, inhibition, competition, anti-complex, multi-component binding, or for example molecular beacon assays. A membrane 10 or substrate is shown in which for example binding spots 32a, 32b are embedded forming arrays 11 in the membrane 10 or substrate. Here, only two binding spots 32a, 32b are presented as part of an array 11. The binding spots 32a, 32b comprise binding sites 31a, 31b, which are designed to bind exclusively to a special target 30a, 30b, their complement. For this, binding sites 31a, 31b are referred to complementary binding sites 31a, 31b. Different targets 30a, 30b can be determined and analyzed by the device 1, each special target 30 having a complementary binding site 31a, 31b within the binding spots 32a, 32b. Generally, the membrane 10 incorporates channels out of pores having sizes preferably in the range of 50 nm to 20 μm through which the fluid 3 flows through the membrane 10. These channels are equipped with features to attain the binding, unbinding etc. mentioned above, as binding spots 32a, 32b for example.

Figures 3, 4:
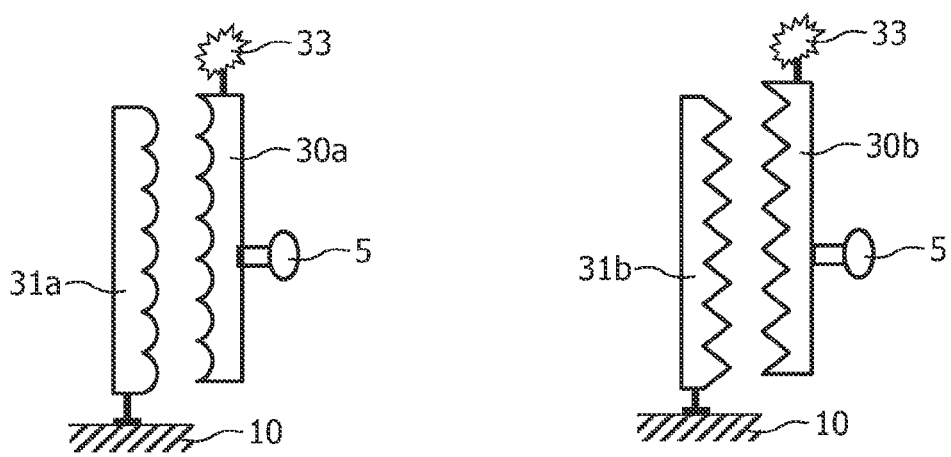

FIG. 3 further explains the process of binding of a target 30a to a binding site 31a by a schematic view. A substrate or membrane 10 is arranged with a special and unique complementary binding site 31a, which is coupled to the substrate or membrane 10. Ideally no other target 30a of another chemical substance may bind to this complementary binding site 31a. The complementary binding site 31a has by way of explanation a special form of a row of semicircles on one side. This form indicates a schematic binding process, the semicircles perfectly fit in a unique way into recesses within the target 30a to create a binding between the target 30a and its complementary binding site 31a. This binding process is similar to the fitting of a key into a lock. The target 30a is by way of example a fragment of a DNA molecule, whereas the complementary binding site 31a is a complementary DNA (c-DNA) molecular fragment. Furthermore, a marker 33 is attached to the target 30a. This marker 33 is for detection in various ways, for instance optical detection as described in FIG. 1. In the case of optical detection the marker 33 is fluorescent, chemiluminescent, radioactive or absorptive. FIG. 3 shows magnetic particle 5 next to target 30. This is to indicate that the movement of particle 5 drags along the target 30. The drag can be by a viscous drag flow, or because particle 5 and target 30 are bound to each other, e.g. via physicochemical or biochemical means. In the case the particles 5 are used for viscous drag, magnetic particles 5 for moving the fluid 3 are preferably removed after a proper mixing and binding is reached, in order not to disturb the marker detection process. In case of a (bio)chemical binding between target 30 and particle 5, the binding can for example be a specific biochemical binding, as in a sandwich format for example. In the latter case, a magnetic particle 5 or bead is attached to the target 30a for realizing a movement of the fluid 3, as will be described below, or as a marker for magnetic detection. In the latter case an optical marker 33 is obsolete.

FIG. 4 further shows a schematic view similar to FIG. 3 with a different target 30b binding to a different complementary binding site 31b. Complementary binding sites 31a and complementary binding site 31b can be arranged in the same substrate or membrane 10, targets 30a and 30b can be arranged in the same fluid 3. Both, the target 30b and its complementary binding site 31b are unique in the understanding that ideally a binding only between them takes place, i.e. no binding between the target 30a and the complementary binding site 31b takes place. Again, a marker 33 is coupled to the target 30b for different ways of detection. The complementary binding site 31b has for demonstrative purposes a saw form different from the semicircle form of the complementary binding site 31a. The target 30b uniquely fitting the complementary binding site 31b has a saw form complementary to the saw form of the binding site 31b. The fluid 3 moving through the device 1 along or through the substrate or membrane 10 permit the targets 30a, 30b to bind or attach to their corresponding complementary binding sites 31a, 31b, respectively.

Figure 5:
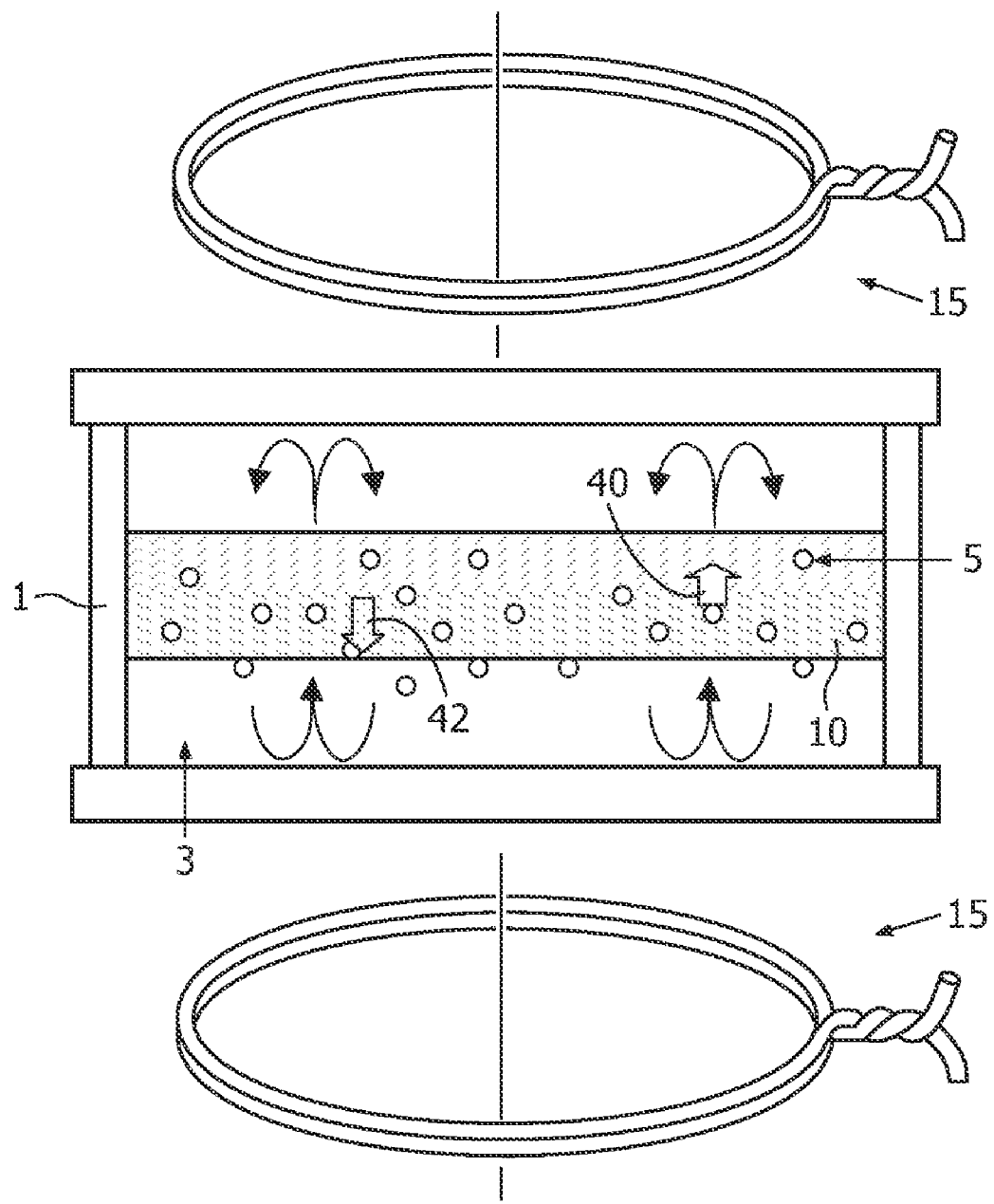

FIG. 5 shows a special embodiment of the invention for detection of targets 30a, 30b by means of a magnetic device. Shown is an exemplary schematic side view of a device 1 for analyzing fluids 3 with two magnetic means 15 generating a magnetic field applied to the device 1. The magnetic means 15 in FIG. 5 are designed as coils, by way of example, other possible designs are electromagnets, permanent magnets, rotating magnets or other devices. One magnetic mean 15 is arranged over the device 1 another magnetic mean 15 is arranged below the device 1 in this arrangement. For the purpose of easy alignment, the magnetic means 15 can be integrated into the device 1. The magnetic field generated has by way of example a field gradient of $\nabla B = 10\text{-}100$ T/m. The device 1 has a porous membrane 10 with bindings sites 31a, 31b for binding targets 30a, 30b. Inside the device 1a fluid 3 comprising targets 30a, 30b and magnetic particles 5 is incorporated. The magnetic particles 5 are also called magnetic beads, which are preferably paramagnetic, superparamagnetic, or ferromagnetic. The average diameter of the magnetic particles 5 is smaller than the average pore size of the membrane 10 in order to allow effective transport of the magnetic particles 5 through the membrane 10. Preferably, the magnetic particles 5 have undergone a size selection, for example by filtering or separation during manufacturing, to minimize the probability that magnetic particles 5 get stuck inside the material of the membrane 10. The outer diameter of the magnetic particles 5 ranges from between a few tens of nanometers to several micrometers, preferably the diameter is >50 nm and <5 µm, most preferably >100 nm and <2 µm. Typically, the magnetic particles 5 comprise cores of magnetic material surrounded by an inert shell made of organic or inorganic material. The shell enhances the stability of the magnetic particles 5 and avoids aggregation or degradation of the magnetic properties of the magnetic particles 5. Further, the shell provides good surface properties, by which the surfaces of the magnetic particles 5 do not stick together and avoid unwanted non-specific binding to substances not planed and to allow the attachment of specific biochemical molecules to the particle surface.

The horizontally arranged magnetic means 15 generate an approximately homogenous magnetic field applied to the magnetic particles 5. The magnetic field exerts a force to the magnetic particles 5 stuck to the targets 30a, 30b which causes the magnetic particles 5 to move in the direction of lower magnetic energy. Not only the magnetic particles 5 are moved through the device 1 but also the targets 30a, 30b connected with the magnetic particles 5 and the fluid 3 surrounding the magnetic particles 5 and the targets 30a, 30b are moved.

The magnetic field is changed frequently, by this the direction of magnetic forces is changed accordingly. FIG. 5 shows an arrow 40 directed upwards denoting magnetically generated flow streamlines pointing in the same direction and exerting forces to the magnetic particles 5 in the same direction. By changing the magnetic field the magnetically generated streamlines change whereby forces to the magnetic particles 5 can be exerted in the opposite direction, indicated by the arrow 42. The fluid 3 is moved through the device 1 upwards and downwards. Thereby, the fluid 3 passes through the membrane 10 dividing the device 1 horizontally from both directions perpendicular to the membrane 10. The movement of the fluid 3 within the device 1 is faster compared to fluid 3 of the state of the art flowing non activated and being influenced essentially by mechanical forces and Brownian motion.

The movement of the fluid 3 supports the mixing of the substances or constituents in the fluid 3. For example, the process of binding of the targets 30a, 30b within the fluid 3 to the magnetic particles 5 within the fluid 3 can be improved and accelerated. This mixing can be executed within the device 1, so an additional process step of mixing outside the device 1 can be saved. Also, the process of binding of the targets 30a, 30b within the fluid 3 to the corresponding unique binding sites 31a, 31b within the membrane 10 can be improved and accelerated. This improvement is coherent as the fluid 3 passes several times the membrane 10 offering a higher probability of binding. The effectiveness of binding is improved, as more magnetic particles 5 bind to the corresponding targets 30a, 30b and more targets 30a, 30b bind to their corresponding binding sites 31a, 31b compared to state of the art using essentially mechanical force. By passing through the membrane 10 the targets 30a, 30b within the fluid 3 bind to corresponding binding sites 31a, 31b within the porous membrane 10, as described in FIG. 3 and FIG. 4 in detail. The more often the targets 30a, 30b pass the membrane 10 the more targets 30a, 30b bind to their unique binding site 31a, 31b. The speed and refresh rate of fluid 3 moving within the device 1 is improved, this means the important duration of the process of analyzing a fluid 3 is shortened.

For further improvement of the binding or the improvement of the kinetics of the assay in the device 1 magnetic particles 5 have a multi-particle structure, such as chains or columns of magnetic particles 5 or beads. This multi-particle structure can be formed by applying a magnetic field to the magnetic particles 5. The multi-particle structures may be chains of magnetic particles, rings of magnetic particles, clusters of magnetic particles or other multi-particle structures. The orientation of the long axis is depending on the orientation of applied magnetic fields. The long axis may be straight or curved. An advantage of using multi-particle structures is that individual particles inside the structures have a higher magnetic moment due to the reduced demagnetising fields. In addition, the total magnetic moments of such structures, and therefore also the magnetic forces or moments, are larger than in case of individual particles 5. The force that can be applied to a magnetic multi-particle 5 structure is given by equation (1):

$$F = \nabla(m \cdot B) \qquad (1)$$

wherein m is the magnetic moment of the multi-particle 5 structure, B the applied magnetic field. For illustration purposes, let us assume a particle moment m that is more or less constant. Then $F = m\nabla B$, with $\nabla B$ the gradient of the applied magnetic field. A chain of, for example, one hundred particles 5 can experience an approximately 100-fold higher force than a single particle 5 or bead due to the higher total magnetic moment m of the multi-particle structure. Multi-particle structures may comprise a combination of large and small particles but may also be structures comprising particles 5 with similar size. Typically, multi-particle structures may comprise two magnetic particles 5 to several 1000 magnetic particles 5 or beads, but even higher numbers are also possible. A chain of magnetic particles 5 experiences approximately the x-fold force in comparison to a single magnetic particle 5 due to the higher magnetic moment of the multi-particle structure, whereby x means the number of magnetic particles 5, as mentioned. One example of a multi-particle structure which can be used is a chain of magnetic particles 5. It is known that magnetic particles 5 form chains when the inter-bead magnetic forces exceed the thermal motion. Magnetizing magnetic particles 5 has the effect of inducing a dipole-dipole interaction between neighbouring magnetic particles 5, which results in the formation of chains of magnetic particles 5 in the direction of the magnetic field lines. Over time the chains interact with each other to form columns. The multi-particle 5 structures that are formed are determined by the applied field pattern, the duration of field application, the modulation frequency, the types of magnetic particles 5 that are used, for example depending on the size, susceptibility, magnetic anisotropy, shape, superparamagnetic or ferromagnetic properties, and the concentration of the magnetic particles 5. The device 1 is provided with means to insert or extract fluids 3 from the chamber inside the device 1, for example to insert a fluid 3, add a reagent, replace the fluid 3 or solution by a washing buffer, etc. Also in those cases, the magnetic particles 5 can help to mix fluids 3 and enhance fluid transport through the membrane 10. Magnetic particles 5 can be supplied to the device 1 in wet or dry state, i.e. from a solution or by dissolving dry magnetic particles 5 containing a reagent into another solution, which is for example the sample fluid 3 to be investigated or an incubation buffer. Reference is made in context of multi-particle structures to EP2005100618 which is incorporated by reference to this description.

Figure 6:
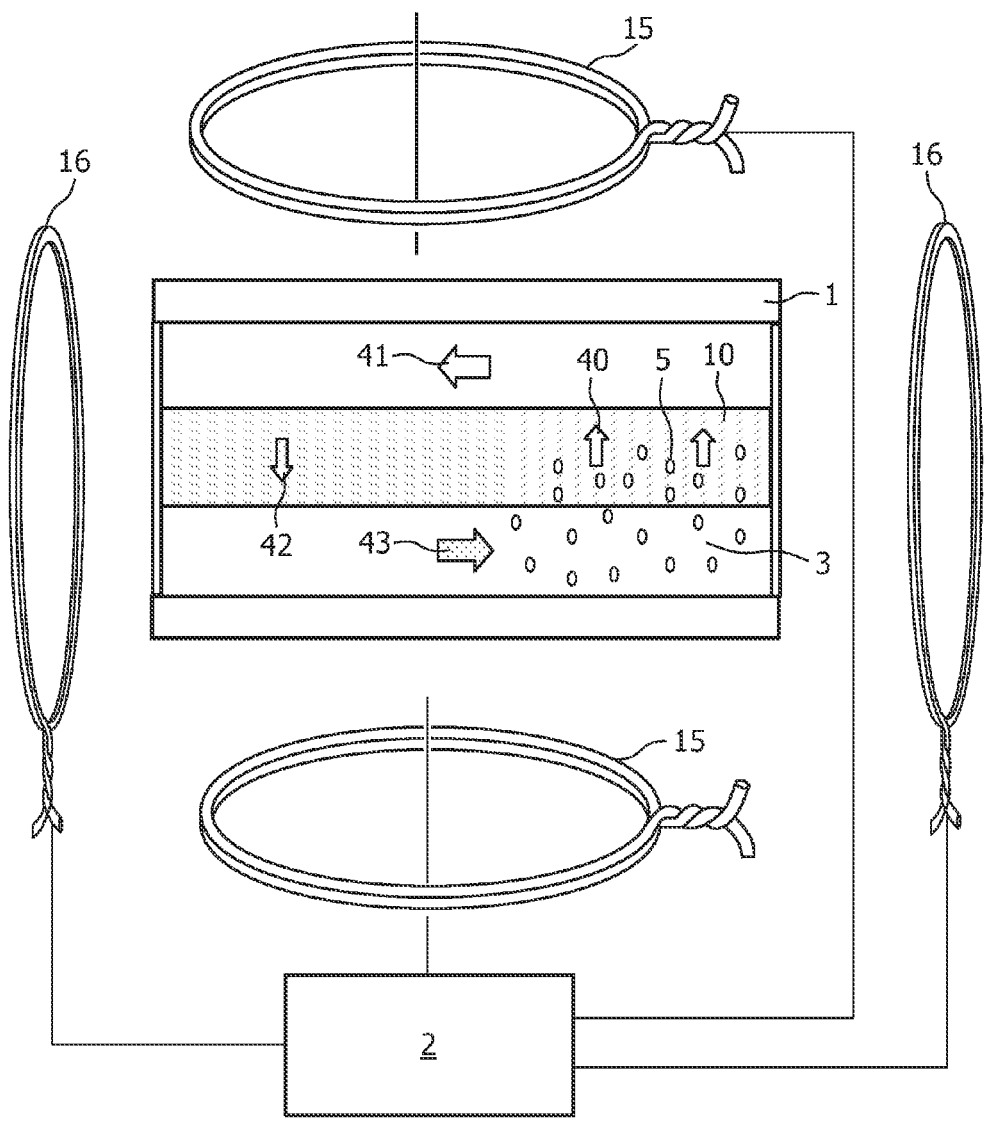

FIG. 6 shows a schematic side view similar to FIG. 5 with four magnetic means 15, 16 arranged at the device 1 similar to FIG. 5. The device 1 is designed similar to FIG. 5 with a membrane 10 dividing the device 1 into two halves horizontally. Two magnetic means 15 are arranged horizontally at opposite sides of the device 1, as described in FIG. 5, in the following horizontal magnetic means 15. Furthermore, two other magnetic means 16 are arranged vertically at opposite sides of the device 1, in the following vertical magnetic means 16. The horizontal magnetic means 15 as well as the vertical magnetic means 16 each generate a magnetic field perpendicular to each other. The horizontal magnetic means 15 exert a force to the magnetic particles 5 in the vertical direction, upwards and downwards, respectively, as indicated by arrows 40, 42. The vertical magnetic means 16 exert a force to the magnetic particles 5 in the horizontal direction to the left and to the right, respectively, as indicated by arrows 41, 43. The flow of the fluid 3 through the device 1 is thereby directed in a horizontal way and in a vertical way, as indicated by the arrows 40, 42 and 41, 43 respectively. A control device 2 is provided which is connected with the magnetic means 15, 16 and designed to control the strength or intensity of the magnetic fields generated by the magnetic means 15, 16. By means of controlling the magnetic means 15, 16 an arbitrary flow through the device 1 is achieved, the fluid 3 can be directed in different directions in dependence of the magnetic field strength or intensity. This especially supports the mixing of the fluid 3 and the binding of targets 30a, 30b to magnetic particles 5 and to binding sites 31.

In a further step, targets 30a, 30b are detected by different means, for example by magnetic field sensors, e.g. a GMR (Giant Magneto Resistive) sensor, Hall sensor, SQUID, or high-frequency coils, or by an optical detector. A GMR registers and measures a magnetic stray field generated by the magnetic particles 5 thereby measuring the amount of magnetic particles 5 within the fluid 3 after mixing or binding as described above is finished. Out of this amount of magnetic particles 5 it is concluded to the amount of targets 30a, 30b to be analyzed which are bound to the magnetic particles 5. In another application an additional marker 33, which is described above of magnetic type, may be of optical type to make an optical detection possible. In this case optical markers 33 are attached to the targets 30a, 30b, and a detection is executed by means of an optical detector, as described in FIG. 1. The higher the detection rate of this optical marker 33 the higher is the concentration of targets 30a, 30b. The optical detection of the targets 30a, 30b can be accomplished at the same time as the targets 30a, 30b move by means of the magnetic means 15, 16.

Figure 7:
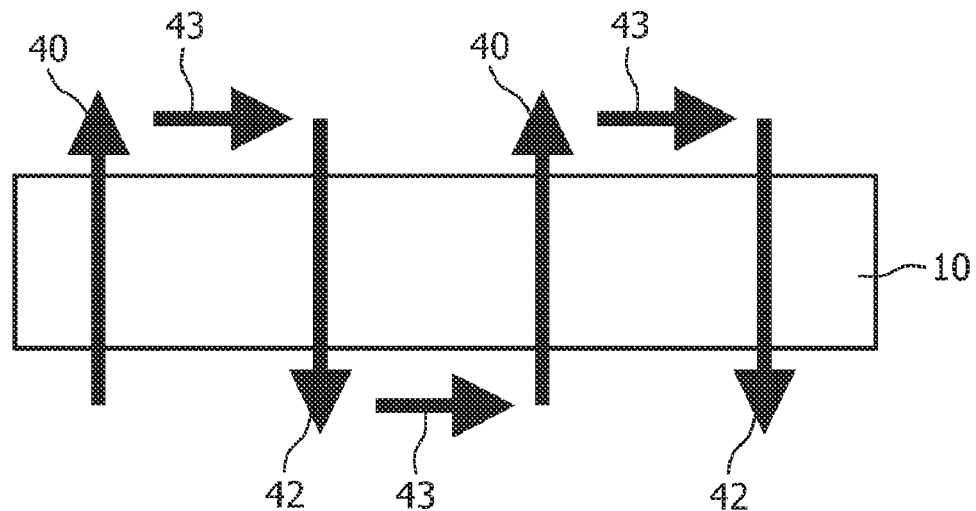
FIG. 7 shows a schematic side view demonstrating another path along which the fluid is moved along and through the membrane.

FIG. 7 shows another schematic side view of the membrane 10 through which and along which fluid 3 is moved. The direction of fluid movement is controlled by the control device 2 in a way that the fluid changes the direction several times. Any direction and change of direction of the fluid can be generated by varying the magnetic field by the control device 2. By example is shown a change in direction of the fluid 3 for six times indicated by the arrows 40 which are directed from the downside to the upside of the membrane 10, the arrows 42 which are directed in the opposite direction, and by the arrows 43 which are directed from left to right along the membrane 10. The control device 2 for instance turns off the magnetic means 15 which generate a magnetic field in the vertical direction when activated by the control means 2 and at the same time activates the magnetic means 16 which generate a magnetic field in the horizontal direction with a distinct intensity. This leads to a magnetic force onto the magnetic particles 5 directed to a horizontal direction, as shown by the arrows 43 pointing from left to right. The control device 2 to this end of changing the intensity of the magnetic field strength for example controls the current which flows through the magnetic means 15, 16. The control device 2 is also designed to control the magnetic means 15, 16 in a way to invert the magnetic fields. Thereby, the direction of fluid 3 can also be controlled to flow from the right side to the left side of the device 1, as already shown by the arrow 41 in FIG. 6.

Figure 8:
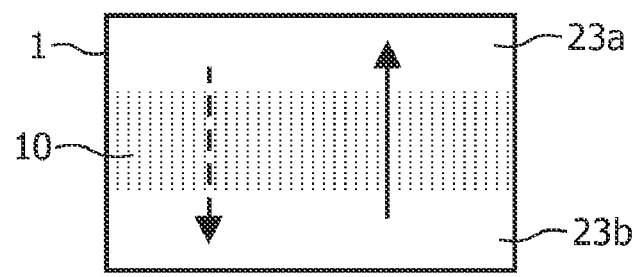
FIG. 8 shows a schematic side view of a closed device with two chambers with a fluid flowing from the first chamber into the second chamber through the membrane and flowing back from the second chamber into the first chamber through the membrane.

FIG. 8 shows a schematic side view of a closed device 1 with two chambers 23a, 23b which are essentially separated by a membrane 10, which is designed as described above. Therefore the device 1 is separated in two parts filled with fluid 3 wherein each part of the device 1 comprises a chamber 23a, 23b. A further number of chambers 23a, 23b can be designed within the device 1. At the left side of the device 1a dashed arrow pointing down indicates a flow of fluid 3 comprising targets 30a, 30b from the first chamber 23a through the membrane 10 into the second chamber 23b, in this illustration a flow of fluid 3 from the top to the bottom of the device 1. The flow of fluid 3 is caused by the magnetic field exerting a force to the magnetic particles 5 or beads incorporated in the fluid, as described above. In one embodiment the magnetic force directed from top to down as shown operates in the left part of the device 1 as shown. In the right part of the device 1a magnetic force is directed from the bottom to the top of the device 1 as shown exerting a force to the fluid 3, indicated by a solid arrow in the right part of the device 1. Thereby, the fluid 3 flows back from the second chamber 23b into the first chamber 23a again through the membrane 10. The two magnetic fields described are generated by two magnetic means 15, 16, which are preferably controlled by a control device. Alternatively, a single magnetic means 15, 16 is provided with the device 1 which is controlled in a way that the magnetic field is alternating leading to a flow of fluid 3 which is directed from top to the bottom at one time and which is directed in the other direction at another time. In another embodiment a single magnetic means 15, 16 is provided which generates a magnetic field only in one direction, e.g. in the vertical direction from top to the bottom as shown in FIG. 8 by the dashed arrow or vice versa and causes a flow in the same direction. The flow back from the second chamber 23b into the first chamber 23a, indicated by the solid arrow, is caused by pressure exerting from the fluid 3 flowing from the first chamber 23a into the second chamber 23b. Fluid 3 in the second chamber 23b is suppressed by fluid 3 from the first chamber 23a and forced to flow into the first chamber 23a. Further magnetic means 15, 16 can be provided.

Figure 9:
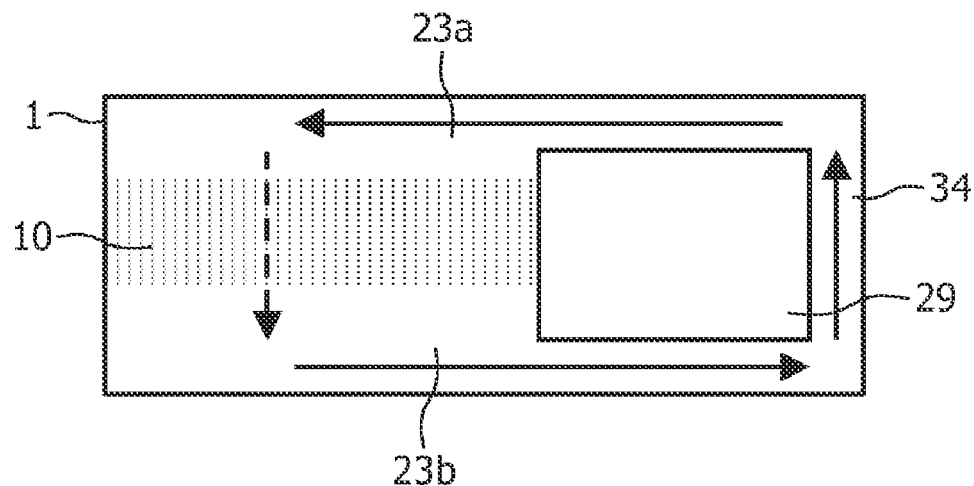
FIG. 9 shows a schematic side view of a closed device with two chambers with a fluid flowing from the first chamber into the second chamber through the membrane and flowing back from the second chamber into the first chamber through a separate channel.
Figure 10:
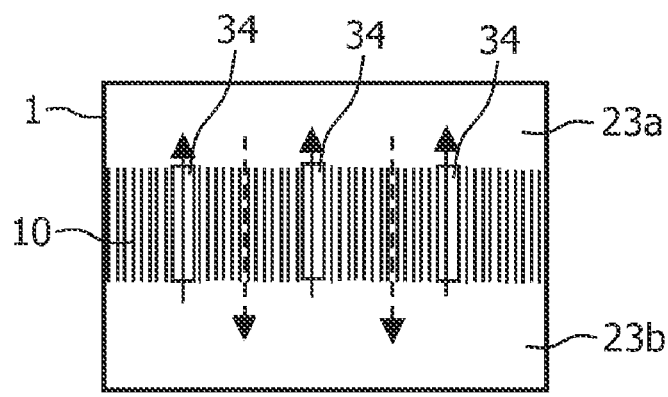
FIG. 10 shows a schematic side view of a closed device with two chambers with a fluid flowing from the first chamber into the second chamber through the membrane and flowing back from the second chamber into the first chamber through separate channels shaped into the membrane.

FIG. 9 shows a schematic side view of a closed device 1 with two chambers 23a, 23b which are in most parts of the device 1 separated by a membrane 10. A magnetic means 15, 16 generates a magnetic field in the device 1 for moving the fluid 3 inside the device 1. Again the dashed arrow indicates the flow of fluid from the first chamber 23a through the membrane 10 into the second chamber 23b. In this embodiment shown in FIG. 9 the first chamber 23a and the second chamber 23b are not separated totally by the membrane 10. Instead, a device is dividing a part of the first chamber 23a from the second chamber 23b, referred to as dividing device 29, which is attached to the membrane 10 and projects through the whole width of the device 1 in direction of the plane of FIG. 9, so that it divides one part of the device 1 with the membrane 10 at the left from the other part of the device 1 at the right without the membrane 10. The dividing device 29 forms one side of a channel within the device 1 which second side is formed by a wall of the device 1. In FIG. 9 the wall forming one side of the channel is the right wall of the device 1. The channel serves for the fluid 3 to flow back from the second chamber 23b at the bottom of FIG. 9 into the first chamber 23a at the top of FIG. 9 and is referred to as backflow channel 34. The flow of the fluid 3 back into the first chamber 23a is again indicated by a solid arrow in the appropriate direction reaching through the backflow channel 34. As an alternative the backflow channel 34 is designed to project through the membrane 10 and is thereby incorporated in the membrane 10. A plurality of backflow channels 34 can be provided in the membrane 10 serving as a duct for fluid 3 through the membrane 10 without passing arrays 11 to bind targets 30a, 30b thereto, shown in FIG. 10. Thus, the backflow channels 34 are not to be mistaken by the equipped channels in the membrane 10 for binding, unbinding etc. described above under FIG. 2. As in the description above the dashed arrows directed from the top of the device 1 characterize the flow of fluid 3 from the first chamber 23a into the second chamber 23b through the membrane 10 passing the channels out of pores, whereby the targets 30a, 30b undergo an action, as binding, unbinding etc. The solid arrows directed from the bottom to the top characterize the flow of fluid 3 through the backflow channels 34 from the second chamber 23b into the first chamber 23a, whereby the targets 30a, 30b undergo no action and only pass the backflow channel 34.

For the purpose of mixing different fluids 3 within the device 1 various fluids 3, at least two fluids 3, are fed to the device 1 of which at least one fluid 3 has to comprise magnetic particles 5. After the mixing procedure the fluids 3 are conducted out of the device 1 or fluids 3 are handled as described above. A mixing function is useful for mixing different reagents of fluid 3 and also for mixing reagents that were dissolved from a dry state into a fluid 3, or for homogenizing the fluid 3 during operation of the device 1. The term reagent denotes a substance to be analyzed irrespective of the state of aggregation, see also definition of the term fluid 3 above.

Non exclusive exemplary areas of application of the invention are bio sensors and molecular diagnostics, rapid and sensitive detection of proteins and nucleic acids in complex biological mixtures, as blood or saliva, on-site testing, diagnostics in centralized laboratories, medical diagnostics, as cardiology, infectious disease, oncology, food and environmental diagnostics.

High-surface-area elements as described can be used for lab-on-a-chip or process-on-a-chip applications wherein a large fluid-to-solid interaction surface is required, e.g. for binding or for material conversion. An example of conversion is an apparatus wherein material is converted by an enzymatic or catalytic reaction at the high-surface-area element. Such a high-surface area element will often not stand alone, but it will be part of a larger apparatus in which more functions are integrated, e.g. elements for sample taking, sample pretreatment, material extraction, etc.

The invention claimed is:

1. A device for analyzing a fluid including magnetic particles and targets bound to the magnetic particles, the device comprising:
    magnetic means configured to generate a magnetic field for exerting a magnetic force on the magnetic particles in the fluid to create movement of the fluid; and
    a membrane comprising at least one binding site for binding the targets and a plurality of channels extending through the membrane, the channels enabling transport of the magnetic particles between chambers separated by the membrane in response to the movement of the fluid through the channels.

2. The device as claimed in claim 1, wherein the magnetic particles are configured as strings of magnetic particles.

3. The device as claimed in claim 1, further comprising:
    at least one backflow channel for conducting fluid that is suppressed by the movement of the fluid pumped through the channel in the membrane.

4. The device as claimed in claim 1, further comprising:
    a control device configured to control the magnetic means to vary the magnetic forces exerted on the magnetic particles for directing the magnetic particles and moving the fluid through the membrane.

5. The device as claimed in claim 4, wherein the control device is further configured to direct the magnetic particles and the fluid through different parts of the membrane.

6. The device as claimed in claim 4, wherein the control device is configured to direct the magnetic particles and the fluid on one side of the membrane through the membrane from a first direction, along the membrane in a second direction, on the opposed side of the membrane through the membrane from a third direction opposite to the first direction, and along the membrane in a fourth direction, thereby creating a circular flow of the magnetic particles and the fluid.

7. The device as claimed in claim 1, wherein the magnetic means comprise wires or coils.

8. The device as claimed in claim 1, wherein the magnetic means comprise electromagnets.

9. The device as claimed in claim 1, wherein the magnetic means comprise permanent magnets.

10. The device as claimed in claim 1, wherein the magnetic means comprise magnets changing their positions relative to the membrane by rotating.

11. The device as claimed in claim 1, wherein the magnetic particles form multi-particle structures.

12. The device as claimed in claim 1, further comprising:
    an optical detector configured for optical detection of the targets and measuring an amount of the targets.

13. The device as claimed in claim 1, wherein a magnetic field generating wire or coil is provided for generating a magnetic field inducing a magnetic stray field of the magnetic particles and a magnetic field sensor for measuring the magnetic stray field.

14. The device as claimed in claim 1, wherein a mechanical stabilizer is arranged at the membrane for improving mechanical stability of the membrane.

15. The device as claimed in claim 1, wherein the membrane has a thickness in a range of 2 to 1000 μm and a pore size of the channels in a range of 50 nm to 20 μm.

16. The device as claimed in claim 1, wherein the magnetic particles are designed as markers for optical detection.

17. A device for analyzing a fluid including magnetic particles and targets to be analyzed bound to the magnetic particles, the device comprising:
    a plurality of magnets configured to generate a magnetic field for exerting a magnetic force on the magnetic particles in the fluid to create movement of the fluid through a membrane separating a plurality of chambers, the membrane having at least one binding site and comprising a plurality of channels extending through the membrane enabling transport of the magnetic particles in response to the movement of the fluid; and
    a control device configured to direct the magnetic particles through the plurality of chambers in different parts of the membrane by varying an intensity of the magnetic field exerted by the plurality of magnets.

18. The device as claimed in claim 17, wherein the control device varies the magnetic field intensity of horizontal magnetic means and of vertical magnetic means.

19. A method for analyzing a fluid containing magnetic particles, the method comprising:
    generating a magnetic field for exerting a magnetic force on the magnetic particles to create movement of the fluid through a membrane separating a plurality of chambers, the membrane having at least one binding site and comprising a plurality of channels extending through the membrane enabling transport of the magnetic particles in response to the movement of the fluid; and varying an intensity of the magnetic field to direct the magnetic particles through different parts of the membrane.

20. The method as claimed in claim 19, further comprising:

removing the magnetic particles for creating a movement of the fluid; and analyzing the fluid by optically measuring of the target bound to binding spots of the membrane.

21. The method as claimed in claim 19, wherein creating a movement of the fluid causes mixing different fluid components within the chambers.

\* \* \* \* \*